United States Patent [19]

Heitz

[11] 4,020,152
[45] Apr. 26, 1977

[54] BARIUM TITANATE AND BARIUM ZIRCONATE IN RADIOLOGICAL CONTRAST PRODUCTS

[75] Inventor: Fernand Alfred Désiré Heitz, Saint-Mande, France

[73] Assignee: Thann & Mulhouse, Thann, France

[22] Filed: Dec. 19, 1973

[21] Appl. No.: 426,016

[30] Foreign Application Priority Data

Dec. 19, 1973 France ............... 73.45166

[52] U.S. Cl. .................. 424/4; 106/137; 106/193 J; 106/209; 106/299; 106/308 C; 106/308 P; 424/360; 424/361; 424/362; 424/363

[51] Int. Cl.$^2$ ................. A61K 29/02

[58] Field of Search ........... 424/4; 106/299, 193 J, 106/209, 137, 308 C, 308 P

[56] References Cited

UNITED STATES PATENTS

| | | | |
|---|---|---|---|
| 1,216,980 | 2/1917 | Gardner | 106/299 |
| 1,396,924 | 11/1921 | Buckman | 106/299 |
| 1,411,839 | 4/1922 | Buckman | 106/299 X |
| 1,429,841 | 9/1922 | Buckman | 106/299 |
| 2,260,826 | 10/1941 | Booge | 106/299 X |
| 2,841,503 | 7/1958 | Graham et al. | 106/299 X |
| 3,592,185 | 7/1971 | Frei et al. | 424/4 X |
| 3,705,140 | 12/1972 | Bernardi et al. | 424/4 X |

FOREIGN PATENTS OR APPLICATIONS

| | | | |
|---|---|---|---|
| 666,592 | 10/1938 | Germany | 424/4 |
| 657,979 | 10/1951 | United Kingdom | 424/4 |

*Primary Examiner*—Albert T. Meyers
*Assistant Examiner*—Vera C. Clarke
*Attorney, Agent, or Firm*—Darby & Darby

[57] ABSTRACT

A radiological contrast product comprising a non-toxic radiopaque salt selected from the group consisting of barium titanate and barium zirconate and a method for conducting radiological examinations of the gastrointestinal tract of a mammal with said product is disclosed herein.

24 Claims, No Drawings

BARIUM TITANATE AND BARIUM ZIRCONATE IN RADIOLOGICAL CONTRAST PRODUCTS

The present invention relates to new radiological contrast products to be administered orally or by rectal injection with a view toward making a radiological examination of the digestive tract and various other organs which are artificially opacified in order to obtain a radiographic image for medical diagnosis.

More specifically, this invention relates to the use of barium salts including oxygen and metallic constituents from Group IV-a of the periodic table as radiological contrast agents.

Radiological examination of the digestive tract consists of administering to the patient a suspension containing elements that are opaque to X-rays, waiting until this mixture has reached the portion of the digestive tract to be examined, and in examining the patient either by means of fluoroscopy or via a transparency produced by X-rays.

The mixture generally utilized heretofore for such radiological examinations has been an aqueous suspension of barium sulphate which may be supplemented by a stabilizing material such as gum arabic. Barium is employed because its large-diameter atoms absorb X-rays.

The use of a barium sulphate suspension as a radiological contrast medium has a certain number of drawbacks which are unavoidable. A principal drawback is that the barium sulphate suspension has poor adhesion to the walls of the digestive tract.

The latter are not sufficiently coated by the contrast agent after its passage, to be properly examined. It is therefore necessary to proceed with radiological examination of the segment of the digestive tract involved, at the very moment that the barium sulphate mixture is passing through this particular segment. At this time the mass of barium sulphate creates a total opacity which appears on fluoroscopic or radiographic examination as a silhouette of uniform shade which does not permit viewing anything except the contours of the organ to be examined, and does not bring out the alterations and gradations on the inner surface of the organ.

One illustration of the lack of adhesion of a barium sulphate suspension is that it is particularly difficult to make radiographs of the aero-digestive crossroads. Patients have difficulty in holding a mouthful of contrast medium at this crossroads for a long time without swallowing. Should the patient swallow the barium sulphate suspension slides over the mucous membrane, practically without coating it. This is probably due to the fact that the walls of the oropharynx and the hypopharynx are abundantly covered with saliva which substantially reduces the adherence of the barium sulphate suspension to the mucous membranes lining these organs.

As a result, radiological examination of this intersection is difficult and leads to mediocre transparencies which do not make for precise diagnosis.

Furthermore, the time required for the barium sulphate mixture to traverse the lumen of the entire digestive tract is always very long, and can take up to several hours.

Radiological examination of the entire digestive apparatus is therefore necessarily fragmentary, requiring a number of operations and considerable loss of time.

According to the present invention, it has been unexpectedly discoverd that certain barium salts, and particularly barium titanantes and barium zirconates function as the basis for an excellent radiological contrast media. Furthermore contrast media based on these compositions permit precise X-ray examinations without out the inherent drawbacks of a barium sulphate suspension.

The toxicity, if any, of products based upon barium salts, is due to the presence of soluble barium ions. The barium salts of this invention do not contain any toxic, soluble barium ion, and it has been affirmed and demonstrated that they are non-toxic. It is however, well known, that alkaline-earth metal titanates and zirconates such as barium titanate and barium zirconate are slowly attacked by acids and that the gastric environment can in certain cases be rather acid. This attack is accelerated as the medium becomes more acidic and in certain instances gastric hyperacidity can therefore facilitate such activity.

It has also been discovered that it is advantageous to combine a certain proportion of a suitable soluble sulphate material with the barium salts described above in preparing a radiological contrast media, with the object of insuring its harmlessness.

It is therefore an object of the present invention to provide a new class of non-toxic radiological contrast agents displaying excellent adhesion and radiological contrast characteristics.

Another aspect of the present invention is the provision of radiological contrast products containing barium salts selected from the class consisting of barium titanates and barium zirconates.

A further aspect of the present invention is to provide radiological contrast compositions based on barium titanate or barium zirconate that are protected against accidental liberation of barium ions in the event that they remain for an abnormally long period of time in the acidic gastric environment.

A still further aspect of the present invention is the provision of processes for preparing the radiological contrast products of this invention.

Another object of the present invention is to provide new procedures for conducting radiological examination of internal body organs in mammals.

The barium salts utilized in the present invention can generally be classified as salts of barium with a metallic element selected from group IV-a of the periodic table and oxygen. Those barium salts which have been found to be especially suitable as radiological contrast agents in the instant invention are pure barium monotitanate, also known as metatitante, of the formula $BaTiO_3$, which appears in the form of a white powder insoluble in water, and barium zirconate ($ZrO_3Ba$).

The invention will now be further described with reference to barium titanate, the preferred barium salt constituent.

Pure barium monotitanate is prepared either by calcination, at a suitable temperature, of a mixture of $TiO_2$ gel with barium carbonate, or a mixture of dry $TiO_2$ with technical barium oxide, or by any other suitable method. A preferred process of preparation of pure barium titanate consists of calcining the double oxalate of titanate and barium of the formula $BaTiO (C_2O_4) 2 \cdot 2H_2O$, and is prepared, for example, by action of a mixture of barium chloride and titanium oxychloride on a solution of oxalic acid.

Barium titanate may be prepared according to the following procedure:

1. — 4.8 liters of a solution of barium chloride containing 494 g of $BaCl_2 \cdot 2H_2O$ is mixed with 1.1 liters of a solution of titanium oxychloride containing 160 g of titanium in the form of $TiO_2$, to yield solution A.

2. — To a reaction vessel (10 liters useful volume) equipped with an agitator, is added 554 g of oxalic acid dihydrate in 3 liters of water. The mixture is heated to 80° C.

3. — Into the same vessel is then introduced (still under agitation), at the rate of 2 liters/hour, all of solution A, the temperature being kept at 80° C. In this way a compound forms, of formula $BaTiO (C_2O_4) 2 \cdot 2H_2O$ (double oxalate of titanium and barium).

4. — The agitation is stopped and after cooling the precipitate is filtered and washed until chlorine ions can no longer be detected in the wash waters.

5. — The double oxalate of titanium and barium, dewatered and washed, is calcined at 1,200° C for 4 hours to yield 445 g of barium monotitanate (or metatitanate) ($TiO_3Ba$) of an 466.7 gm theoretical yield, or an actual yield of 95.8%. Analysis of the finished product gives the following results:

| | | |
|---|---|---|
| Free BaO | | none |
| % $TiO_2$ | | 34.7 |
| % combined BaO | | 65.7 |
| Fe | | 5 ppm |

Alternatively it is possible to start with a raw material containing the double oxalate titanium of and potassium (industrial product) from which is prepared an aqueous solution. a solution of (200g/l) barium chloride is introduced into the double oxalate solution in order to precipitate the double oxalate of titanium and barium.

After filtration and washing, the precipitate is calcined as above to yield barium titanate.

A study of the acute toxicity of barium titanate administered orally was made on the mouse and on the rat.

The administration by esophageal sound of an aqueous suspension in various concentrations, of barium titanate to male, Charles River $CD_1$ mice of 24 to 26 g yielded the following results:

| Number of mice | Barium titanate g/kg (orally administered) | 4 hrs. | Mortality after 24 hrs. | 72 hrs. |
|---|---|---|---|---|
| 3 | 1 | 0 | 0 | 0 |
| 3 | 2 | 0 | 0 | 0 |
| 3 | 4 | 0 | 0 | 0 |
| 10 | 8 | 0 | 0 | 0 |
| 10 | 12 | 0 | 0 | 1 |
| 10 | 16 | 0 | 2 | 5 |

Substantially the same tests were conducted in rats. In the rat studies no signs of toxicity were observed. The $LD_{50}$ for barium titanate was found to be about 3g/kg. Substantially the same tests were carried out with barium zirconate and it was also found to be non-toxic when orally administered as above. It can therefore be concluded that barium titanate and barium zirconate are substantially non-toxic substances, and at the dosage levels used for radiological examination of the digestive tract according to the instant invention are totally lacking in toxicity.

Comparative clinical experiments conducted on the qualities of barium sulphate as opposed to barium titanates and barium zirconates, as contrast agents reveal an undisputed superiority for the barium salts of this invention.

Barium titanate adheres quite well to the walls of the digestive tract, which are coated, after passage of the mixture, with uniform thin layers; the adhesion of these layers persists for about 10 to 15 minutes, thereby providing two significant advantages.

The first advantage is that is it is possible to continue the radiological study for a long time after ingestion. The second advantage has a considerable effect on the precision of the diagnosis.

When the barium salts of this invention are employed as the contrast agents it becomes possible to make radiological examinations of the various parts of the digestive tract immediately after passage of the opaque mass of the contrast agent in the part under consideration, which is not the case with barium sulphate. Furthermore, this examination of the organ walls which are covered with thin layers of contrast agent provides information, not only on the contour of the organ under consideration, but also on the internal relief of the organ. The physician can see perfectly, all of the mucous relief of the entire digestive tract, as well as the finest morphological or pathological alterations, lesions, (even minimal ones like exulcerations), and, naturally, all "hypic" lesions such as ulcers, hypertrophies, and the like regardless of their location on the organ.

The result is that the use of barium titanate, or barium zirconate, either alone or in combination with the soluble sulphate salts according to this invention considerably widens the field of medical investigation, on the one hand by permitting the investigator to obtain more precise and detailed images, and on the other hand by enabling a more leisurely examination of the organs through which the radiological contrast agent travels rapidly, such as the aero-digestive cross-roads, (e.g. the crossing points of the pharnyx and the larynx.)

Finally, it has appeared that, in addition to the adhesive qualities described above, the barium salts of this invention have another unexpected advantage. The replacement of barium sulphate by barium titanate also accelerates the transit of the contrast media through the digestive tube to such an extent that a full examination of the latter can be carried out in about thirty minutes. A full examination with barium sulphate can take up to 8 days due to its slow traverse of the lumen of the gastrointestinal tract.

The barium titanate or barium zirconate salts of the invention are used in the form of a liquid suspension, generally aqueous and concentrated, but dilutable as desired. It is advantageous to add a synthetic or naturally occurring stabilizing agent such as a methyl or ethyl cellulose, gum arabic, gelatin or agar-agar.

The radiological contrast suspensions of the invention may contain between about 2% and 20%, percent of a stabilizing agent.

By reason of its adhesive properties, barium titanate can be used for gastric mucographs in quantities much smaller than those required with barium sulphates, or about three times less. As little as one ounce of a solution containing 50% percent of $BaTiO_3$ can be administered to provide an effective contrast agent for this purpose.

Clinical tests have been made with suspensions of barium titanate and barium zirconate made by mixing 2 to 4 parts by weight of titanate (or zirconate) in 2 to 20 parts by weight of water containing 2% gum arabic.

The following examples are designed to demonstrate the effectiveness of the contrast agents according to the present invention.

PHARYNGEOGRAPHY

The contrast product used was powdered barium titanate, diluted in an aqueous solution of 2% gum arabic.

The solution was prepared prior to each examination in the following proportions:

2 ounces of barium titanate powder were combined with one and one half ounces of an aqueous 2% gum arabic solution. The homogeneity of this solution is obtained by stirring with the aid of a small spoon.

The examination takes place as follows:

Generally one ounce of the mixture is administered orally to the patient who swallows once.

It is rarely necessary to make the patient ingest the remainder of the prepared solution, that is to say a maximum of about 3 ounces, since the product adheres firmly to the recipient organ serving to prepare it for radiographic examination.

Regardless of the organ to be examined or even when dealing with a hyper-salivating patient, a normal or tumoral aero-digestive cross-roads, or the seat of a post-radiotherapeutic epithelite, or even in the case of an uncooperative patient who ignores the order not to swallow, excellent results are obtained. In almost every instance the following structures will receive and retain an adequate amount of the radiological contrast solution to permit excellent radiological examination: base of tongue, epiglottis, valleculae, folds, piriform sinuses and even mucous relief of the cervical esophagus, thereby overcoming the well known difficulties of examining these organs by radiography.

These results are the consequence of the durable and tenacious adherence of the product of this invention to the mucous membranes, embodying a uniform coating that remains in position for some time. The physician generally speaking, can take whatever time he needs in order to produce the various views and functional maneuvers necessary to a complete examination.

It is also possible to carry out several successive examinations after the development of the first X-ray plates, since the barium titanate coating will adhere to the mucous membranes of most of the above-mentioned organs for about ten minutes or more. The examination is reliable, and easily reproducible in time with the same results.

In cases of swallowing the wrong way (windpipe — always unpredictable) bronchial inundation has rarely been observed because the quantity of the dosage is small, and the solution which is passed by effraction, adheres to the tracheal walls without going beyond the middle tracheal region, and without reaching the pulmonary alveoles.

STOMACH RADIOGRAPHY

Eleven ounces of a solution of barium titanate prepared as in the preceding example was administered to a patient. The radiological contrast medium had reached the stomach and coated the gastric mucosa in about 5 minutes after ingestion.

A radiographic image of a stomach coated with a conventional barium sulphate suspension, was compared with that obtained by examination of the stomach coated with the instant barium titanate suspension. The barium sulphate suspension resulted in a mediocre micrograph, with dense opacity, not easily passed by high-kilovolt X-rays, and not providing any information on the contours of the organ. The examination using barium titanate enabled detailed inspection of all the mucous relief of the organ.

ADMINISTRATION OF BARIUM ZIRCONATE EXAMPLE

The preparation was the same as before for pharyngography with barium titanate. The results were also the same with the exception that the products adhere better than the barium sulfate but not as well as barium titanate and not as long (some minutes instead of half an hour).

In order to eliminate the possibility of any toxic effects resulting from attack on the barium titanate or barium zirconate suspension by gastric secretions of hydrochloric acid, a predetermined proportion of a non-toxic, soluble sulphate material may be added to the barium radiological contrast agents of the invention.

Thus, if the barium titanate should begin to decompose slowly, giving off soluble barium ions the latter are immediately reprecipitated by the $SO_4$ ions present, and form insoluble barium sulphate. It is necessary that the sulphate selected have a solubility higher than that of barium sulphate. The soluble sulphates of the invention are generally selected from among the soluble sulphates of alkali metals and alkaline earth metals. The sulphates of sodium, potassium and calcium are especially useful in the invention.

In the broad concept of the invention calcium sulphate is added to the barium titanate in a proportion of from about 0.1% to about 15% calcium sulphate to barium titanate. Prefereably between about 0.1 and 4% of sulfate salt is employed with respect to the barium titanate, or other barium salt.

The combined barium-calcium salt compositions are prepared in the dry state by mixing, which may or may not follow a preliminary grinding of the two constituents.

The following examples are cited by way of illustration of the preceding procedure.

EXAMPLE 1

Into a mixing vessel with horizontal arms is introduced 10 kg of powdered barium titanate and 300 g of ground, anhydrous sodium sulphate. These ingredients are mixed together for one half hour, and the mixture finely ground in the micronizer. A fine white powder is obtained having an actual density of 4.8.

This powder, when placed in a suspension in a hydrochloric acid medium does not liberate soluble barium ions.

EXAMPLE 2

300 grams of barium titante is suspended in 1 liter water containing sufficient hydrochloric acid to have a pH on the order of 2. The resulting product is filtered, washed and dried at 120° C for 8 hours. To the powder is added in a mixing vessel, a quantity of calcium sulphate $SO_4Ca \cdot 2H_2O$ equal to 4% by weight with respect to the barium titanate. This mixture is dried by atomization then ground. The percentage composition of the powder obtained is as follows:

TiO$_2$ 33.4%;
BaO 63.2%;
SO$_4$Ca 3.1%;

This powder, suspended in a hydrochloric acid medium does not liberate soluble barium ions.

The X-ray diffraction diagram obtained of this product, according to the usual method, displays the following known ray characteristics of TiO$_3$Ba wave length diffraction.

1.634 angstroms
1.642 angstroms
1.998 angstroms
2.018 angstroms
2.840 angstroms

EXAMPLE 3

To 10 liters of water containing 200 grams of gum arabic is added 10 kilograms of barium titanate having a ratio of TiO$_2$/BaO = 3.0, and 400 grams of calcium sulphate (SO$_4$Ca·2H$_2$O). This suspension is dispersed at a high speed in Cowles disc mixer for about 20 minutes. The composition thus obtained is ready for ingestion.

Clinical experiments using the above mentioned compositions of barium titanate (or barium zirconate) and calcium sulphate in aqueous suspensions have revealed that these compositions have identical qualities as contrast agents as those demonstrated for barium titanate or barium zirconate, when they are employed alone.

The adherence of the combined titanate-sulphate compositions to the walls of the digestive tube is remarkable, and makes possible extremely precise radiographs of all parts of the digestive tube.

The suspensions of the above compositions are prepared by mixing 2 to 4 parts by weight of the barium titanate — soluble sulphate composition in 2 to 20 parts by weight of water optionally containing about 2% of a stabilizing agent which is preferably gum arabic.

The stomach radiographs made with such suspensions are of superior quality to those obtained with barium sulphate, in that they provide precise information on all of the mucous relief of the organ.

Experiments have shown that barium titanates in which the TiO$_2$/BaO ratio was not equal to 1, as in pure barium metatitanate, but higher than 1, for example, equal to 1.2 or to 2 and even 3, had all the advantages of the metatitanate and thus came within the scope of the present invention. These titanates also satisfy the exigencies of toxicity and are useful in the instant invention.

Beyond a ratio of TiO$_2$/BaO = 3, the titanates obtained no longer offer the same remarkable properties as contrast agents.

Compositions of these barium titanates with soluble sulphates, particularly sodium or calcium sulphate, in proportions ranging up to 0.1% to 15% by weight of sulphate with respect to the barum titanate have also been prepared and tested for use in aqueous contrast media. The results obtained were excellent, permitting detailed examination of the organs to be studied.

The preparation, the composition and the use of the combined sulphate - barium titanate radiological mixtures can be illustrated by the following information presented in the form of examples:

a. Example For Pharynogography

A paste is prepared by combining 15 grams of barium titanate and calcium sulphate (consisting of 96% barium titanate and 4% calcium sulphate by weight) with 10 ml. of water. This relatively thick paste material can be orally administered to the patient and permits a detailed examination of the pharynx by radiography Generally between about 10 and 20 grams of paste material must be administered in order to effect an X-ray examination of the pharynx.

b. Composition For Examination of the Stomach 85 grams of barium titanate calcium sulphate mixture (81 parts by weight BaTiO$_3$ and 3.5 parts by weight calcium sulphate) which has been put into a dispersion of 280 ml. of water containing 30 grams of gum arabic previously dissolved in the water. The quantities of barium titanate or mixture of the barium titanate (TiO$_3$Ba and sulphate) used for the examination of the pharynx, the esophagus, the stomach and the intestine is generally between about 8 to about 150 grams and preferably between 10 and 100 grams.

As previously indicated, the barium zirconates, and in particular, the zirconate of the formula ZrO$_3$Ba had the same unexpected properties of opacification to X-rays and adherence to the walls of the digestive tube, and of acceleration of the transit of the radiological contrast medium that were described for barium titanate.

Barium zirconate, ZrO$_3$Ba, can be prepared as follows:

50 of zirconium oxide and 72 kg of anhydrous barium carbonate are mixed together in a conventional mixer. This mixture is introduced into a calcination furnace where it is kept at 1,150° C for 4 hours. After cooling and grinding, 100 kg of ZrO$_3$Ba was obtained in the form of a white powder.

Compositions of these zirconates of barium and soluble sulphates, particularly sodium or calcium sulphate, in proportions ranging up to about 15% by weight of sulphate with respect to the barium zirconate, were prepared in a manner analogous to that described for barium titanate.

The properties of the barium zirconates as a contrast agent were tested successfully: the radiographs obtained by the administration of aqueous suspensions of these compositions of barium sulphate as the radiological contrast agent.

The adherence of these compositions with barium zirconate base is as remarkable as that of the compositions with barium titanate base.

The radiological contrast compositions of this invention may be administered orally in the form of a paste solution, cream, gel or suspension, or may be introduced by injection into the rectum.

What is claimed is:

1. An orally administrable radiological contrast product comprising an aqueous suspension containing from two to twenty parts by weight of barium titanate of the formula BaTiO$_3$ in from two to twenty parts by weight of water and a stabilizing agent selected from the group consisting of methyl cellulose, ethyl cellulose, gum arabic, gelatin and agar-agar.

2. An orally administrable radiological contrast product comprising an aqueous suspension containing from two to twenty parts by weight of barium zirconate of the formula BaZrO$_3$ in from two to twenty parts by weight of water and a stabilizing agent for said suspension selected from the group consisting of methyl cellulose, ethyl cellulose, gum arabic, gelatin and agar-agar.

3. The radiological contrast product according to claim 1 wherein said stabilizing agent is gum arabic.

4. The radiological contrast product according to claim 2 wherein said stabilizing agent is gum arabic.

5. An orally administrable nontoxic radiological contrast composition for radiological examinations, comprising an aqueous suspension consisting essentially of an effective amount of a barium titanate having a $TiO_2/BaO$ ratio between 1:1 and 3:1 and from about 0.1% to about 15% by weight of said barium titanate of a soluble sulphate selected from the group consisting of an alkali metal sulphate and alkaline earth metal sulphate having a higher solubility in water than barium sulphate.

6. The composition according to claim 5, wherein the soluble sulphate is sodium sulphate.

7. The composition according to claim 5 wherein the sulphate is calcium sulphate.

8. The composition according to claim 5 wherein said sulphate comprises between about 0.1 and 4% by weight of the barium titanate.

9. A radiological contrast product comprising from 2 to 4 parts by weight of barium zirconate and from 2 to 20 parts by weight of water and gum arabic as a stabilizer for said contrast product.

10. A non-toxic radiological contrast composition for radiological examination comprising an orally administrable aqueous suspension of an effective amount of barium zirconate and from about 0.1 to about 15% by weight of said barium zirconate of a soluble sulphate selected from the group consisting of an alkali metal sulphate and an alkaline earth metal sulphate having a higher solubility in water than barium sulphate.

11. The composition according to claim 10 wherein the sulphate is sodium sulphate.

12. The composition according to claim 10 wherein the sulphate is calcium sulphate.

13. The composition according to claim 10 wherein the soluble sulphate comprises between 0.1 and 4% by weight of said barium zirconate.

14. A method of preparing a composition for radiological examination which comprises mixing an effective amount of a barium salt selected from the group consisting of barium titanate having a $TiO_2/BaO$ ratio of between 1:1 and 3:1 and barium zirconate with about 10% by weight of said barium salt of a non-toxic soluble sulphate selected from the group consisting of an alkali metal sulphate and an alkaline earth metal sulphate having a higher solubility in water than barium sulphate, grinding the mixture to a fine powder and suspending said powder in water.

15. The method of preparing a composition for radiological examination according to claim 14 wherein the quantity of sulphate introduced is between about 0.1 and 4% by weight of said barium salt.

16. The method according to claim 15 wherein the sulphate is sodium sulphate.

17. The method according to claim 15 wherein the sulphate is calcium sulphate.

18. A method for making a radiological examination of the digestive tract of a mammal which comprises orally administering to said mammal an effective quantity for radiographic examination of an aqueous suspension of a barium salt selected from the group consisting of a barium titanate having a $TiO_2/BaO$ ratio between 1:1 and 3:1

19. The method of claim 18 wherein said aqueous suspension also includes a soluble sulphate selected from the group consisting of an alkali metal sulphate and an alkaline earth metal sulphate having a higher solubility in water than barium sulphate.

20. The method according to claim 19 wherein the soluble sulphate is sodium sulphate.

21. The method according to claim 19 wherein the sulphate is calcium sulphate.

22. A method for making a radiographic examination of the digestive tract of a mammal which comprises rectally administering to said mammal an effective quantity for radiographic examination of an aqueous suspension of a barium salt selected from the group consisting of a barium titanate having a $TiO_2/BaO$ ratio between 1:1 and 3:1 and barium zirconate.

23. The method of claim 22 wherein said aqueous suspension also includes a soluble sulphate selected from the group consisting of an alkali metal sulphate and an alkaline earth metal sulphate having a higher solubility in water than barium sulphate.

24. A radiological contrast agent in powder form consisting of an effective amount of a radioopaque barium salt selected from the group consisting of a barium titanate having a $TiO_2/BaO$ ratio between 1:1 and 3:1 and a barium zirconate and from 0.1 to about 15% by weight of said barium salt of a water soluble non-toxic sulphate selected from the group consisting of an alkali metal sulphate and an alkaline earth metal sulphate having a solubility in water superior to barium sulphate.

* * * * *